United States Patent
Traneus et al.

(10) Patent No.: US 11,786,753 B2
(45) Date of Patent: Oct. 17, 2023

(54) METHOD, COMPUTER PROGRAM PRODUCT AND COMPUTER SYSTEM FOR RADIOTHERAPY PLANNING, AND RADIOTHERAPY DELIVERY SYSTEM

(71) Applicant: RaySearch Laboratories AB (Publ), Stockholm (SE)

(72) Inventors: Erik Traneus, Uppsala (SE); Bjorn Hardemark, Enskededalen (SE); Kjell Eriksson, Balsta (SE)

(73) Assignee: Raysearch Laboratories AB (publ), Stockholm (SE)

( * ) Notice: Subject to any disclaimer, the term of this patent is extended or adjusted under 35 U.S.C. 154(b) by 0 days.

(21) Appl. No.: 17/906,453

(22) PCT Filed: Mar. 16, 2021

(86) PCT No.: PCT/EP2021/056609
§ 371 (c)(1),
(2) Date: Sep. 15, 2022

(87) PCT Pub. No.: WO2021/185797
PCT Pub. Date: Sep. 23, 2021

(65) Prior Publication Data
US 2023/0115222 A1    Apr. 13, 2023

(30) Foreign Application Priority Data
Mar. 18, 2020    (EP) .................... 20163840

(51) Int. Cl.
*A61N 5/10* (2006.01)
*G16H 20/40* (2018.01)

(52) U.S. Cl.
CPC ......... *A61N 5/1031* (2013.01); *A61N 5/1048* (2013.01); *G16H 20/40* (2018.01);
(Continued)

(58) Field of Classification Search
CPC ...... A61N 5/10–1084; A61N 2005/1085–1098
See application file for complete search history.

(56) References Cited

U.S. PATENT DOCUMENTS

2019/0022409 A1    1/2019 Vanderstraten et al.
2019/0022411 A1    1/2019 Parry et al.
(Continued)

FOREIGN PATENT DOCUMENTS

| CN | 110582325 A | 12/2019 |
| CN | 110709134 A | 1/2020 |

(Continued)

OTHER PUBLICATIONS

International Search Report & Written Opinion, European Patent Office, dated May 14, 2021, Rijswijk, Netherlands.
(Continued)

*Primary Examiner* — Thaddeus B Cox
(74) *Attorney, Agent, or Firm* — Norén's Patentbyrå AB

(57) ABSTRACT

A radiotherapy treatment planning method for achieving a FLASH radiotherapy treatment plan involves optimizing the plan using an optimization problem that has been designed to maximize the part of the irradiation that will be delivered under FLASH conditions, in particular to an organ at risk, to minimize the damage to the organ at risk.

12 Claims, 1 Drawing Sheet

(52) U.S. Cl.
CPC ............... *A61N 2005/1034* (2013.01); *A61N 2005/1087* (2013.01)

(56) References Cited

U.S. PATENT DOCUMENTS

| | | |
|---|---|---|
| 2019/0060667 A1 | 2/2019 | Vanderstraeten et al. |
| 2019/0255354 A1 | 8/2019 | Nordstrom et al. |
| 2020/0298025 A1* | 9/2020 | Cooley, III .......... A61N 5/1079 |

FOREIGN PATENT DOCUMENTS

| | | |
|---|---|---|
| WO | 2018152302 A1 | 8/2018 |
| WO | 2018202285 A1 | 11/2018 |
| WO | 2019192951 A1 | 10/2019 |

OTHER PUBLICATIONS

Vozenin et al., The advantage of Flash radiotherapy confirmed in mini-pig and cat-cancer patients. Clinical Cancer Research, American Association for Cancer Research, 2019, 25 (1), pp. 35-42.
Vozenin, M.-C., et al., "Biological benefits of Ultra-high dose Rate Flash radiotherapy: Sleeping beauty awoken", Clinical Oncology, 2019, vol. 31, No. 7, pp. 407-415.
Office action, dated Feb. 7, 2023, Japanese Patent Office.
Office action dated Nov. 8, 2022, Chinese Patent Office.

* cited by examiner

METHOD, COMPUTER PROGRAM PRODUCT AND COMPUTER SYSTEM FOR RADIOTHERAPY PLANNING, AND RADIOTHERAPY DELIVERY SYSTEM Method, computer program product and computer system for radiotherapy planning, and radiotherapy delivery system

TECHNICAL FIELD

The present invention relates to radiotherapy planning and in particular to a method for radiotherapy treatment planning for generating treatment plans involving irradiation under FLASH conditions, a computer program and a computer system for performing such planning and a radiotherapy delivery system for delivering such treatment to a patient.

BACKGROUND

Radiotherapy treatment always involves delivering dose outside of the target, to healthy tissue or organs at risk, and therefore there is always a risk that healthy organs or tissue are damaged by the radiation. One emerging treatment method that appears to involve less undesired damage is FLASH therapy, which involves treatment at a much higher dose rate than conventional therapy, for example, 70 Gy/s. In the literature related to FLASH, various lower limits to the dose rates are suggested, such as at least 40 Gy/s or 50 Gy/s. If, for example, a dose of 20 Gy is to be delivered with a dose rate of 70 Gy/s, the whole dose will be delivered in 0.29 s. In contrast, conventional radiotherapy treatment is delivered at much lower dose rates, a typical dose rate for conventional radiotherapy treatment being a few Gy per minute. It has been found that with FLASH therapy the damage done to healthy tissue by a particular dose is lower than with conventional therapy, while the effect on the target, that is, the tumorous tissue response, remains the same, although the mechanisms behind this are not yet fully understood.

Vozenin et al.: The advantage of FLASH radiotherapy confirmed in mini-pig and cat-cancer patients, HAL Id: hal-01812514, https://hal-univ-rennesl.archives-ouvertes.fr/hal-01812514v2 confirmed that the differential effect between normal tissue and tumor subjected to FLASH therapy, that had previously been shown for mice, could also be seen in pigs and cats.

Dose delivered under FLASH conditions to risk organs causes less damage by a factor which may be approximately 30%. Hence, the iso-effective harmful dose to an organ at risk is higher than the physical dose, in this example, 1/0.7 times the physical dose.

Published U.S. patent application Ser. No. 2019/0022411 also relates to FLASH therapy, which is said to give reduced side effects for the same dose. Dose rates of 40 Gy/s or more, up to more than 500 Gy/s are mentioned, allowing a dose fraction to be delivered in a fraction of a second. The radiation may be delivered by a number of beams from different angles. The problem of overlapping beams near the target, resulting in a higher dose than desired to the regions in which there is overlap is discussed. The planning method is focused on minimizing the overlap between beams outside of the target by considering the geometry of the patient and target and the beam angles.

SUMMARY OF THE INVENTION

It is an object of the invention to provide FLASH therapy that utilizes the positive effects of this therapy form in the best possible way by reducing damage to healthy tissue while maintaining the response in the target.

The invention relates to a computer-based method of creating a radiation therapy treatment plan for a patient, said plan involving FLASH therapy provided as at least a first beam such that a portion of the irradiation will be delivered as FLASH irradiation, said method comprising defining a desired dose distribution including a target dose prescription, and optimizing the plan using an optimization problem designed to minimizing the dose to at least one organ at risk while maximizing the FLASH portion of the dose to at least one organ at risk while respecting the target dose prescription.

As will explained below, when delivering FLASH therapy to a patient, because of the nature of the dose delivery, a portion of the irradiation dose will be delivered to each voxel at a lower non-FLASH dose rate. The Total Effective Dose (TED) is defined as the sum of the iso-effective doses from the FLASH portion and the non-FLASH portion. As explained above, FLASH dose involves a much higher dose rate than conventional therapy, for example, 40 Gy/s or 50 Gy/s or even up to more than 500 Gy/s. This means that a typical dose to a patient can be delivered much faster than with conventional therapy. Because irradiation delivered under FLASH conditions causes less damage to the tissue than conventional, non-FLASH irradiation, for the same dose, the invention aims at maximizing the portion of the irradiation that is delivered under FLASH conditions, to at least one organ at risk. This will minimize the damage to the organ at risk, assuming that the dose remains the same. At the same time, the optimization must also ensure that the target receives the prescribed dose.

A key factor in dose planning is how to achieve the dose distribution within the patient that best matches the desired dose distribution. Optimizing based on a dose distribution typically achieves a more optimal dose distribution than considering only patient geometry and beam geometry to avoid overlap between the beams. Hence, the method according to the invention will result in better treatment plans than the methods known in the prior art.

As will be discussed below, the dose rate and the time structure of the dose delivery are both important for achieving the effect of FLASH therapy.

In preferred embodiments employing proton radiation, the optimization problem is defined to optimize with respect to relative biological effectiveness—RBE—dose. RBE is a measure of the damage caused by a particular dose relative to a reference dose, which is different for different types of radiation, and for FLASH and non-FLASH respectively. For photons under non-FLASH conditions the RBE is 1. For non-FLASH proton therapy current clinical practice is to us a factor 1.1, which means that 70 Gy delivered as non-FLASH proton radiation corresponds to 77 Gy delivered as non-FLASH photon radiation.

In some embodiments, the optimization problem comprises an objective function designed to maximize the FLASH portion of the plan. Alternatively, the optimization problem comprises an objective function designed to minimize the non-FLASH portion of the plan. As will be understood, this is just two different ways of expressing the same objective, since the total dose will be the sum of the FLASH portion and the non-FLASH portion.

The optimization problem may be designed to maximize the FLASH portion or minimize the non-FLASH portion, as the case may be, by optimizing or selecting one or more of the following:

spot size,
spot shape
spot placement
spot weights
beam arrangement with respect to energy, number of beams and/or direction of beams Alternatively, or in addition, the optimization problem may be defined so as to maximize the FLASH portion or minimize the non-FLASH portion by optimizing or selecting by optimizing or selecting an order for scanning the spots.

It is possible to optimize a plan having at least a first and a second beam, both beams including FLASH portions. These may be delivered by a rotating gantry, or by two radiation sources positioned at an angle from each other. In the latter case, the two beams may be delivered with a very short interval between them, so as to enhance the FLASH effect.

It is also possible to optimize a plan including at least a first and a second beam, wherein the first beam includes a FLASH portion and the second beam only includes a conventional non-FLASH irradiation. In this case, the optimization problem is preferably arranged to minimize the total effective dose from both the FLASH therapy portion and the conventional therapy portion of the first beam and the second beam in at least one organ at risk.

The invention also relates to a computer program product comprising computer-readable code which, when run in a processor in a computer will cause the processor to perform the method according to any one of the embodiments discussed above. The computer program product may include non-transitory storage means having the code stored thereon. The invention also relates to a computer system comprising a processor, at least one data memory and a program memory, wherein the program memory comprises such a computer program product.

The invention also relates to a system for delivering radiotherapy treatment to a patient, comprising a radiation source. The radiation source may be arranged in any suitable way, for example in a gantry or realized by a fixed beam line, wherein the radiation source is arranged to provide radiation at a dose rate high enough to provide FLASH treatment to the patient, said system further comprising a computer for controlling the system, the computer comprising a processor and a memory comprising a treatment plan obtained through an embodiment of the method discussed above.

BRIEF DESCRIPTION OF DRAWINGS

The invention will be described in more detail in the following, by way of examples and with reference to the appended drawings.

DETAILED DESCRIPTION OF EMBODIMENTS

In FLASH therapy, the radiation dose of an entire therapy session may be delivered as one ultra-high dose in less than a second, or a number of beams having a high dose rate and being delivered with short time intervals between them. Short in this context should be taken to mean much shorter than the normal time required for rotating a gantry from one beam angle to another, which is normally around 30 seconds. A high dose rate in this context is assumed to be above 40 Gy/s but may be considerably higher. This means that the delivery time for a certain dose with FLASH therapy will be considerably lower than with conventional therapy. For example, in conventional therapy, a dose of 2 Gy may be delivered as continuous radiation over a period of approximately one minute, whereas a FLASH dose of 2 Gy will be delivered in the fraction of a second, 1/20 of a second if the dose rate is 40 Gy/s. Since FLASH therapy means that the effective dose to the target is close to the physical dose while the effective dose to the surrounding healthy tissue is lower by a factor of maybe 30%, such therapy is advantageous in that it reduces the damage to healthy tissue. The time frame for FLASH dose delivery should be somewhere on the order of magnitude between millisecond and second.

Figure 1:
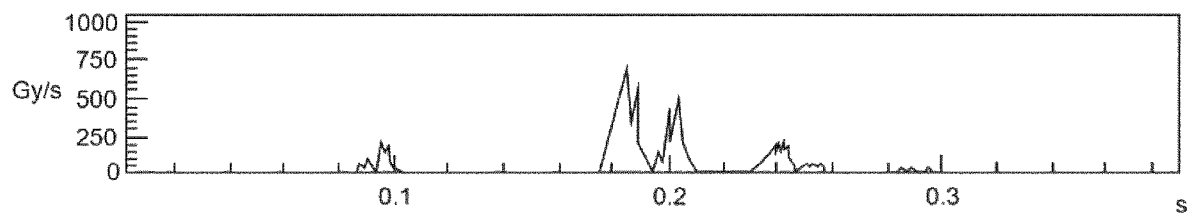
FIG. 1 is a flow chart of the method according to the invention.

FIG. 1 illustrates, by way of example, the time structure for a FLASH irradiation of one individual voxel in the patient, for example a voxel within the organ at risk, as the dose rate (cGy/s) per time unit. The irradiation is delivered as a pencil beam scan, which means that part of the delivery will only partially hit the voxel, whereas other parts will hit close to the center of the voxel. The ones that only partially hit the voxel will result in a lower dose rate, and therefore a lower dose, to the voxel, typically a non-FLASH level whereas the ones that hit close to the center of the voxel will have a higher effective dose rate for the voxel and therefore give a higher dose, which will constitute the FLASH component. In the example shown in FIG. 1, there is first a non-flash component at 0.1 s, then two higher peaks, with a sufficiently high dose rate to constitute FLASH irradiation, in this example momentarily reaching up to about 7000 Gy/s, between 0.18 and 0.2 s and finally a lower, non-FLASH component at around 0.22 s. As will be understood, there may be more, or fewer of both FLASH and non-FLASH components, but in practice there will always be at least one of each. A similar time structure for a conventional non-FLASH dose delivery would be a substantially straight line at, for example, 2 Gy, for a longer period of time, for example one minute.

In the general case, the Total Effective Dose TED for an organ at risk may be expressed in terms of the following equation:

$$TED = x*D(\text{non-FLASH}) + y*D(\text{FLASH})$$

where D(non-FLASH) is the physical non-FLASH dose component to the voxel and D(FLASH) is the physical FLASH dose component. x and y are factors modelling the RBE for the respective component. This means that x and y express the total effective dose from the non-FLASH component and the FLASH component, respectively, relative to the physical dose of that component. A typical value for y is 0.7. For photons, x=1. for charged particles, x is somewhat higher than 1, for example 1.1 for protons.

Figure 2:
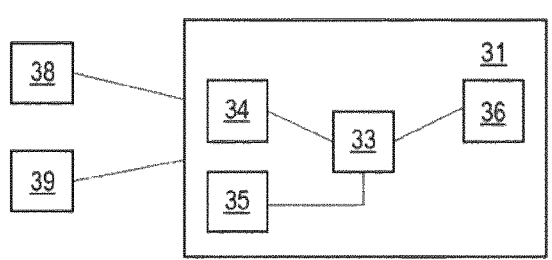
FIG. 2 illustrates by way of example the time structure of dose delivery by pencil beam scanning.

According to the invention, therefore, the FLASH therapy treatment is planned by means of optimization of an optimization problem designed to provide the desired dose to the target with a high dose rate as discussed above, in a short period of time, typically less than 1 s, while keeping the total effective dose to the surrounding tissue at an acceptable level for healthy tissue, including any organs at risk. This is done, in part, by utilizing the fact that the total effective dose from the FLASH component is lower than the total effective dose from the non-FLASH component, relative to the respective actual dose component. The dose may be delivered as one beam or as a number of beams. To achieve this, the optimization problem includes an objective function designed to maximize the FLASH component in at least one organ at risk. As will be understood, this may also be formulated as minimizing the non-FLASH component in the at least one organ at risk. As is common in the art, this objective may be achieved by in different ways, including optimizing one or more of the following:

the spot scan order, and/or
the spot placement and/or
the spot weights and/or
the beam arrangement, with respect to the energy, directions and/or number of beams.
the spot shape FIG. 2 is a schematic flow chart of the method according to the invention. In a first step S21, the desired dose distribution for a particular patient is defined. In a second step S22, an optimization problem is defined. In a third step S13, dose optimization is performed based on the optimization problem.

In a first embodiment, the optimization problem is designed to output a plan for FLASH therapy only. The FLASH therapy may be delivered in one or more beams from the same or different angles. In a second embodiment, the optimization problem is designed to output a plan that combines at least one beam involving FLASH therapy and at least one beam at conventional non-FLASH dose rates.

In particular, the optimization should result in a treatment plan including a FLASH component in areas where there are risk organs. By replacing conventional treatment with FLASH treatment in these areas, the damage to the tissue in these areas can be reduced. This is especially important in areas where the dose is so high that damage to one or more risk organs can be expected. The risk is particularly high near the target, where beams aimed at the target from different angles may overlap.

As discussed above, the optimization problem is preferably designed such that the FLASH effect is maximized while respecting the target dose prescription. For proton irradiation this means that the optimization problem may be designed to also consider the Relative Biological Effectiveness (RBE) of the dose, which for FLASH therapy is a function of both the dose rate and the time structure of the radiation, as well as other factors such as tissue type and type of irradiation. Other factors may also be considered. The time frame for dose delivery should be somewhere on the order of magnitude between millisecond and second.

The aim of the treatment plan optimization is to achieve the desired dose in the target while minimizing the total effective dose in at least one organ at risk, where the total effective dose is the sum of the FLASH dose component, adjusted for the FLASH effect factor, and the conventional therapy component of the treatment. One way of implementing this would be to use different types of scorers in the dose engine. For example, in a Monte Carlo dose engine this would involve scoring voxel-wise energy deposition time traces resolved into time bins of for example approximately milliseconds.
dirty dose concept, where dirty in this context can mean non-FLASH dose in the organ at risk.

A Monte Carlo simulation follows the path of different particles, including the direction and energy of the particle, the type of particle and the physical effect of the particle. The skilled person would be able to implement this in other types of dose engine.

Figure 3:
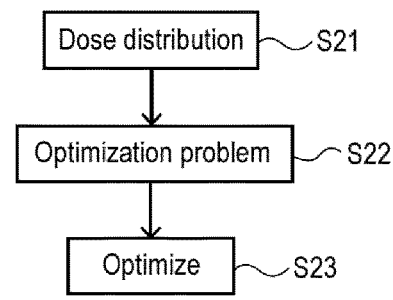
FIG. 3 illustrates schematically a computer system which may be used in dose planning according to the invention.

FIG. 3 is a schematic representation of a computer system in which the inventive method may be performed. A computer 31 comprises a processor 33, a first and a second data memory 34, 35 and a program memory 36. Preferably, one or more user input means 38, 39 are also present, in the form of a keyboard, a mouse, a joystick, voice recognition means or any other available user input means. The user input means 38, 39 may also be arranged to receive data from an external memory unit.

The first data memory 34 comprises necessary data for performing the method, typically including desired dose distribution and segmented patient image. The second data memory 35 holds other data, such as RBE information. The first program memory holds a computer program arranged to make the computer perform the method steps according to some embodiment of the invention.

As will be understood, the data memories 34, 35 as well as the program memory 36 are shown and discussed schematically. There may be several data memory units, each holding one or more different types of data, or one data memory holding all data in a suitably structured way, and the same holds for the program memories. Both the program and the data can be found in one or more memories within the computer system or in another unit that is accessible from the computer system.

Figure 4:
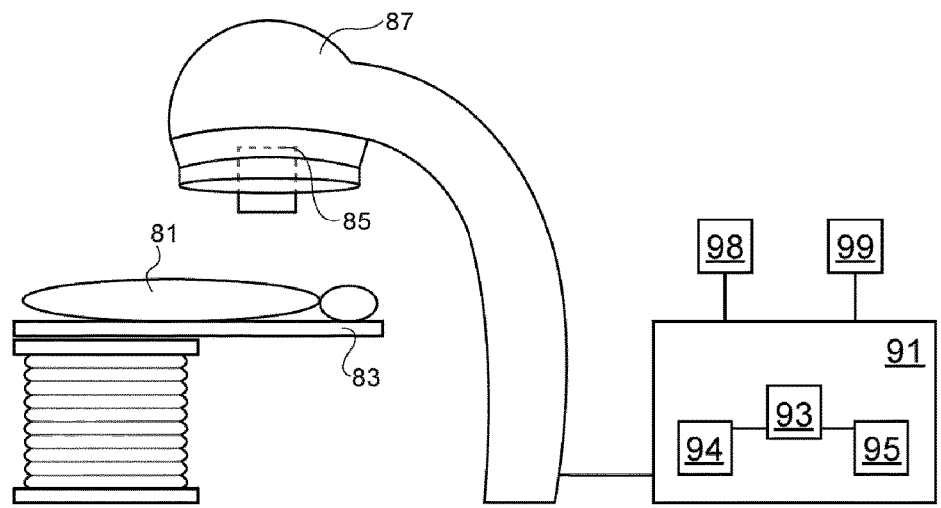
FIG. 4 illustrates a delivery system which may be used for dose delivery according to the invention.

FIG. 4 is an overview of a system 80 for radiotherapy treatment and/or treatment planning. As will be understood, such systems may be designed in any suitable way and the design shown in FIG. 4 is only an example. A patient 81 is positioned on a treatment couch 83. The system comprises an imaging/treatment unit having a radiation source 85 mounted in a gantry 87 for emitting radiation towards the patient positioned on the couch 83. Typically, the couch 83 and the gantry 87 are movable in several dimensions relative to each other, to provide radiation to the patient 81 as flexibly and correctly as possible. These parts and their functions are well known to the skilled person. A main difference between the system used in the context of the invention and a conventional radiotherapy delivery system is that the system according to the invention is adapted to deliver much higher dose rates that what is done according to conventional radiotherapy. Suitable magnitudes of the dose rate are discussed above.

A number of passive devices provided to shape the beam laterally and in depth are typically present and will not be discussed in more detail here. Means are arranged for providing a grid of beams, for example in the form of a grid block, or means for providing pencil beams. The system also comprises a computer 91 which may be used for radiotherapy treatment planning and/or for controlling radiotherapy treatment. As will be understood, the computer 91 may be a separate unit not connected to the imaging/treatment unit.

The computer 91 comprises a processor 93, a data memory 94, and a program memory 95. Preferably, one or more user input means 98, 99 are also present, in the form of a keyboard, a mouse, a joystick, voice recognition means or any other available user input means. The user input means may also be arranged to receive data from an external memory unit.

The data memory 94 comprises clinical data and/or other information used to obtain a treatment plan, or related to the plan itself. Typically, the data memory 94 comprises one or more patient images to be used in treatment planning according to embodiments of the invention. The program memory 95 holds at least one computer program arranged to cause the processor to control the delivery system according to the optimized treatment plan.

As will be understood, the data memory 94 and the program memory 95 are shown and discussed only schematically. There may be several data memory units, each holding one or more different types of data, or one data memory holding all data in a suitably structured way, and the same holds for the program memories. One or more memories may also be stored on other computers. The computer may also be arranged to perform the optimization.

The invention claimed is:

1. A computer-based method of creating a radiation therapy treatment plan for a patient, the plan involving FLASH therapy provided as at least a first beam such that a portion of irradiation will be delivered as a FLASH irradiation portion having a higher dose rate than 40 Gy/s, the method comprising:
    defining a desired dose distribution including a target dose prescription,
    optimizing the plan using an optimization problem designed to maximize the FLASH irradiation portion to at least one organ at risk while respecting the target dose prescription;
    generating a computer-readable file including the optimized plan; and
    transmitting the computer-readable file to a recipient to be used in a system for delivering FLASH radiotherapy treatment to a patient in accordance with the optimized plan.

2. The method of claim 1, wherein the optimization problem is defined to optimize with respect to relative biological effectiveness (RBE) dose.

3. The method of claim 1, wherein the optimization problem comprises an objective function designed to maximize the FLASH irradiation portion of the plan.

4. The method of claim 1, wherein the optimization problem comprises an objective function designed to minimize a non-FLASH irradiation portion of the plan.

5. The method of claim 1, wherein the optimization problem is defined so as to maximize the FLASH irradiation portion or minimize a non-FLASH irradiation portion by optimizing or selecting spot size, spot shape and/or spot placement.

6. The method of claim 1, wherein the optimization problem is defined so as to maximize the FLASH irradiation portion or minimize a non-FLASH irradiation portion by optimizing or selecting at least one of
    spot weights and/or
    a beam arrangement with respect to energy, number of beams and/or directions of beams.

7. The method of claim 1, wherein the optimization problem is defined so as to maximize the FLASH irradiation portion or minimize a non-FLASH irradiation portion by optimizing or selecting an order for scanning spots.

8. The method of claim 1, wherein the plan includes at least a first and a second beam, each delivered as FLASH irradiation.

9. The method of claim 1, wherein the plan involves a first beam including a FLASH therapy portion and a second beam including only a non-FLASH therapy portion, the optimization problem being arranged to minimize a total effective dose from both the FLASH therapy portion and the non-FLASH therapy portion of the first beam and the second beam in the at least one organ at risk.

10. A computer program product comprising a non-transitory computer readable storage medium having program instructions embodied therewith which, when run in a processor in a computer will cause the processor to perform the steps of the method of claim 1.

11. A computer system comprising a processor, at least one data memory and a program memory, wherein the program memory comprises a computer program product according to claim 10.

12. A system for delivering radiotherapy treatment to a patient, comprising a radiation source in a gantry, wherein the radiation source is arranged to provide radiation at a dose rate high enough to provide FLASH treatment to the patient, the system further comprising a computer for controlling the system, the computer comprising a processor, wherein the computer comprises a memory comprising a treatment plan obtained through the method according to claim 1.

* * * * *